US011643692B2

(12) United States Patent
Magliocco et al.

(10) Patent No.: US 11,643,692 B2
(45) Date of Patent: May 9, 2023

(54) METHOD OF DISTINGUISHING LUNG SQUAMOUS CELL CARCINOMA FROM HEAD AND NECK SQUAMOUS CELL CARCINOMA

(71) Applicant: H. Lee Moffitt Cancer Center and Research Institute, Inc., Tampa, FL (US)

(72) Inventors: Anthony M. Magliocco, Orlando, FL (US); Soner Altiok, Tampa, FL (US); Farah K. Khalil, Tampa, FL (US); Yin Xiong, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 870 days.

(21) Appl. No.: 16/534,337

(22) Filed: Aug. 7, 2019

(65) Prior Publication Data

US 2019/0360028 A1 Nov. 28, 2019

Related U.S. Application Data

(63) Continuation of application No. PCT/US2018/019307, filed on Feb. 23, 2018.

(60) Provisional application No. 62/462,561, filed on Feb. 23, 2017.

(51) Int. Cl.
| | |
|---|---|
| *C12Q 1/6886* | (2018.01) |
| *G16H 50/30* | (2018.01) |
| *G06F 18/2135* | (2023.01) |
| *C12Q 1/6827* | (2018.01) |

(52) U.S. Cl.
CPC ......... *C12Q 1/6886* (2013.01); *C12Q 1/6827* (2013.01); *G06F 18/2135* (2023.01); *G16H 50/30* (2018.01); *C12Q 2600/112* (2013.01)

(58) Field of Classification Search
CPC ............ C12Q 1/6886; C12Q 2600/112; G06F 18/2135; G16H 50/30
See application file for complete search history.

(56) References Cited

U.S. PATENT DOCUMENTS

2011/0263444 A1 10/2011 Noguchi et al.

OTHER PUBLICATIONS

Seike M et al (2009) MiR-21 is an EGFR-regulated anti-apoptotic factor in lung cancer in never-smokers. Proc Natl Acad Sci U S A 106(29):12085-12090.
Mountzios G et al (2010) Histopathologic and genetic alterations as predictors of response to treatment and survival in lung cancer: a review of published data. Crit Rev Oncol Hematol 75(2):94-109.
Helland A, Brustugun OT (2009) Lung cancer in smokers and never-smokers. Tidsskr Nor Laegeforen 129(18):1859-1862.
Rudin CM et al (2009) Lung cancer in never smokers: molecular profiles and therapeutic implications. Clin Cancer Res 15(18):5646-5661.
Toh CK et al (2006) Never-smokers with lung cancer: epidemiologic evidence of a distinct disease entity. J Clin Oncol 24(15):2245-2251.

(Continued)

*Primary Examiner* — Joseph G. Dauner
(74) *Attorney, Agent, or Firm* — Michele L. Lawson; Smith & Hopen, P.A.

(57) ABSTRACT

A method of distinguishing between lung squamous cell carcinoma and head and neck squamous cell carcinoma using a 22-gene biomarker signature is presented.

9 Claims, 5 Drawing Sheets

(56) References Cited

OTHER PUBLICATIONS

O'Donnell RK, Kupferman M, Wei SJ, et al. Gene expression signature predicts lymphatic metastasis in squamous cell carcinoma of the oral cavity. Oncogene 2005;24:1244-51.

Nishizuka S, Chen ST, Gwadry FG, et al. Diagnostic markers that distinguish colon and ovarian adenocarcinomas: Identification by genomic, proteomic, and tissue array profiling. Cancer Res 2003;63:5243-50.

Giordano TJ, Shedden KA, Schwartz DR, et al. Organ-specific molecular classification of primary lung, colon, and ovarian adenocarcinomas using gene expression profiles. AmJPathol 2001;159:1231-8.

Ramaswamy S, Tamayo P, Rifkin R, et al. Multiclass cancer diagnosis using tumor gene expression signatures. Proc Natl Acad Sci US A 2001;98:15149-54.

International Search Report and Written Opinion issued by the International Searching Authority dated Jul. 11, 2018 for International priority application No. PCT/US18/19307.

Vachani et al. A10-Gene Classifer for Distinguishing Head and Neck Squamous Cell Carcinoma and Lung Squamous Cell Carcinoma. Clin Cancer Res, May 15, 2007, vol. 13, No. 10, pp. 2905-2915.

Lal A. et al., (2013) A gene expression profile test to resolve head & neck squamous versus lung squamous cancers, Diagn Pathol, 8:44.

Talbot, SG et al. (2005) Gene expression profiling allows distinction between primary and metastatic squamous cell carcinomas in the lung, Cancer Research, 65(8):3063-71.

International Preliminary Report on Patentability issued by the International Bureau dated Sep. 6, 2019 for International priority application No. PCT/US18/19307.

cutoff:

Head & Neck:     PC1< -7.01 & PC2 ≥ 1.816

|  |  |  | classified type | | | |
|---|---|---|---|---|---|---|
| dataset | # samples | actual type | Head & Neck | Lung | sensitivity | specificity |
| TCC | 38 | Head & Neck | 33 | 3 | 86.84% | |
| TCC | 268 | Lung | 14 | 254 | | 94.78% |
| GEO | 130 | lung | 0 | 130 | | 100.00% |
| TCGA | 134 | lung | 0 | 134 | | 100.00% |
| GEO | 96 | Head & Neck | 88 | 8 | 91.67% | |

| # | 22-gene signature for classifying squamous lung cancer vs. squamous head-and-neck cancer | Gene Title |
|---|---|---|
| 1 | ADH1B | Alcohol Dehydrogenase 1B (Class I), Beta Polypeptide |
| 2 | AGTR2 | Angiotensin II Receptor Type 2 |
| 3 | ALDH1A2 | Aldehyde Dehydrogenase 1 Family Member A2 |
| 4 | AQP4 | Aquaporin 4 |
| 5 | C4BPA | Complement Component 4 Binding Protein Alpha |
| 6 | CACNA2D2 | Calcium Voltage-Gated Channel Auxiliary Subunit Alpha2delta 2 |
| 7 | CLDN18 | Claudin 18 |
| 8 | CTSE | Cathepsin E |
| 9 | FGG | Fibrinogen Gamma Chain |
| 10 | KRT14 | Keratin 14 |
| 11 | LMO3 | LIM Domain Only 3 |
| 12 | LRP2 | LDL Receptor Related Protein 2 |
| 13 | PGC | Progastricsin |
| 14 | PLA2G1B | Phospholipase A2 Group IB |
| 15 | SCN7A | Sodium Voltage-Gated Channel Alpha Subunit 7 |
| 16 | SCTR | Secretin Receptor |
| 17 | SFTPA2 | Surfactant Protein A2 |
| 18 | SFTPB | Surfactant, pumonary-associated protein B |
| 19 | SFTPC | Surfactant Protein C |
| 20 | SFTPD | Surfactant Protein D |
| 21 | SSTR1 | Somatostatin Receptor 1 |
| 22 | TCF21 | Transcription Factor 21 |

METHOD OF DISTINGUISHING LUNG SQUAMOUS CELL CARCINOMA FROM HEAD AND NECK SQUAMOUS CELL CARCINOMA

CROSS REFERENCE TO RELATED APPLICATIONS

This application is a continuation of and claims priority to International Patent Application No. PCT/US2018/019307, filed Feb. 23, 2018 which claims priority to U.S. Provisional Patent Application No. 62/462,561, entitled "Method of Distinguishing Lung Squamous Cell Carcinoma from Head and Neck Squamous Cell Carcinoma", filed on Feb. 23, 2017, the contents of each of which are herein incorporated by reference.

FIELD OF INVENTION

This invention relates to tumorigenic assays. Specifically, the invention provides a method of distinguishing between lung squamous cell carcinoma and head and neck squamous cell carcinoma using a 22-gene signature.

BACKGROUND OF THE INVENTION

Lung cancer is the most common cause of mortality worldwide and the most common risk factor for the development of lung cancer is smoking. (Seike M et al (2009) MiR-21 is an EGFR-regulated anti-apoptotic factor in lung cancer in never-smokers. Proc Natl Acad Sci USA 106(29): 12085-12090; Mountzios G et al (2010) Histopathologic and genetic alterations as predictors of response to treatment and survival in lung cancer: a review of published data. Crit Rev Oncol Hematol 75(2):94-109).

Lung squamous cell carcinoma (LSCC), accounts for 28-52% of lung cancers in smokers but only 5.9-18% in never-smokers. (Helland A, Brustugun O T (2009) Lung cancer in smokers and never-smokers. Tidsskr Nor Laegeforen 129(18): 1859-1862; Rudin C M et al (2009) Lung cancer in never smokers: molecular profiles and therapeutic implications. Clin Cancer Res 15(18):5646-5661; Toh C K et al (2006) Never-smokers with lung cancer: epidemiologic evidence of a distinct disease entity. J Clin Oncol 24(15): 2245-2251).

Smoking is also a risk factor for the development of head and neck squamous cell carcinoma (HNSCC). 5% to 15% of patients with HNSCC developed lung metastases. (O'Donnell R K, Kupferman M, Wei S J, et al. Gene expression signature predicts lymphatic metastasis in squamous cell carcinoma of the oral cavity. Oncogene 2005; 24:1244-51). An estimated 61,760 head and neck cancer cases were diagnosed in 2016. More than 90% of head and neck cancers are HNSCC, and 5-15% of HNSCC patients will develop lung metastasis.

The distinction between a lung metastasis and a 2nd primary LSCC can at times be made based on clinical grounds, when there is evidence of multiple pulmonary nodules. However, in patients with a history of HNSCC or a current HNSCC, presenting with a solitary lung nodule, this distinction is very difficult, unless there is a significant difference in the histologic grade of both tumors. Premalignant respiratory epithelial changes, if found in the vicinity of the LSCC are very helpful in this decision.

Patients with early-stage LSCC have a significantly better prognosis than patients with metastatic HNSCC and the correct diagnosis has practical importance for choice of therapy. Classification of human tumors based on the origin of human carcinoma cell lines has been shown by previous gene expression studies. (Nishizuka S, Chen S T, Gwadry F G, et al. Diagnostic markers that distinguish colon and ovarian adenocarcinomas: identification by genomic, proteomic, and tissue array profiling. Cancer Res 2003; 63:5243-50; Giordano T J, Shedden K A, Schwartz D R, et al. Organ-specific molecular classification of primary lung, colon, and ovarian adenocarcinomas using gene expression profiles. Am J Pathol 2001; 159:1231-8; Ramaswamy S, Tamayo P, Rifkin R, et al. Multiclass cancer diagnosis using tumor gene expression signatures. Proc Natl Acad Sci USA 2001; 98:15149-54).

The inventors have used gene expression profiling to compare HNSCC and LSCC in identifying a specific number of differentially expressed genes, which ultimately can prove practical in distinguishing metastatic HNSCC from primary LSCC. The Principal Component Analysis (PCA) has shown high accuracy in classifying patients with HNSCC and LSCC with 22 genes.

SUMMARY OF INVENTION

Primary squamous cell carcinoma (SCC) arising in the lung is morphologically indistinguishable from primary SCC arising in the head and neck area. SCC arising in the head and neck location can metastasize to the lungs and it becomes increasingly difficult to diagnose primary SCC from metastatic SCC in such situations. The inventors have developed and validated a 22-gene signature that distinguishes SCC arising in the lung from SCC arising in the Head and Neck area.

In an embodiment, a method for treating and distinguishing between lung squamous cell carcinoma (LSCC) and head and neck squamous cell carcinoma (HNSCC) in a patient is presented comprising: obtaining a sample from the patient; determining expression levels of two or more genes in the sample selected from the group consisting of ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21; performing Principal Component Analysis (PCA) on the expression levels of the at least two or more genes to obtain a first Principal Component Analysis score (PCA1) and a second Principal Component Analysis score (PCA2); wherein a diagnosis of HNSCC is given if the PCA1 is below a first calculated cutoff of −7.01 and the PCA2 is above or equal to a second calculated cutoff of 1.816, wherein a diagnosis of LSCC is given if the PCA1 is above the first calculated cutoff and the PCA2 is below the second calculated cutoff; and treating the patient using surgery or chemotherapy depending on the diagnosis.

The method can further comprise diagnosing the sample as squamous cell carcinoma (SCC) prior to obtaining the expression levels of the at least two or more genes. The sample may be taken from a solitary lung nodule of the patient who has a history of or currently has HNSCC.

The at least two or more genes can include all of the following genes to arrive at a 22-gene signature: ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21.

Treatment for the diagnosis of LSCC is surgery in the form of a lobectomy with hilar and mediastinal lymph node dissection, adjuvant chemotherapy or immunotherapy while treatment for the diagnosis of HNSCC is surgery in the form of a pulmonary metastasectomy.

In another embodiment, a method of treating and determining progression of HNSCC in a patient is presented comprising: obtaining a sample from the patient; determining expression levels of two or more genes in the sample selected from the group consisting of ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21; performing Principal Component Analysis (PCA) on the expression levels of the at least two or more genes to obtain a first Principal Component Analysis score (PCA1) and a second Principal Component Analysis score (PCA2); wherein the HNSCC has progressed from a primary site if the PCA1 is below −7.01 and the PCA2 is above or equal to 1.816; and treating the HNSCC by pulmonary metastasectomy wherein the surgery removes a wedge-shaped section of a lung.

The method can further comprise diagnosing the sample as squamous cell carcinoma (SCC) prior to obtaining the expression levels of the at least two or more genes. The sample may be taken from a solitary lung nodule of the patient who has a history of or currently has HNSCC.

The at least two or more genes can include all of the following genes to arrive at a 22-gene signature: ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21.

In another embodiment, a method of determining primary tumor site in a patient having cancer is presented comprising: obtaining a sample from the patient; determining expression levels of two or more genes in the sample selected from the group consisting of ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21; performing Principal Component Analysis (PCA) on the expression levels of the at least two or more genes to obtain a first Principal Component Analysis score (PCA1) and a second Principal Component Analysis score (PCA2); wherein the patient is diagnosed with primary LSCC if the PCA1 is above −7.01 and the PCA2 is below 1.816; and treating the LSCC with surgery in the form of a lobectomy with hilar and mediastinal lymph node dissection, adjuvant chemotherapy or immunotherapy.

The method can further comprise diagnosing the sample as squamous cell carcinoma (SCC) prior to obtaining the expression levels of the at least two or more genes. The sample may be taken from a lymph node or other metastatic site of the patient who has a history of or currently has HNSCC.

The at least two or more genes can include all of the following genes to arrive at a 22-gene signature: ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. Where particular values are described in the application and claims, unless otherwise stated, the term "about" meaning within an acceptable error range for the particular value should be assumed. As used herein, "about" refers to ±10%.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "agent" as used herein describes a composition, compound, chemical or extract that can be administered or tested by the present invention as a modulator of a gene. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof. "Agent" is used interchangeably herein with "compound", "composition", "chemical", "drug", and "extract".

"Subject" is used to describe an animal, preferably a mammal, more preferably a human, to whom treatment is administered, including prophylactic treatment with the compositions of the present invention. "Subject" and "patient" are used interchangeably herein.

The genes of the present invention may serve as biomarkers for (1) the diagnosis of disease; (2) the prognosis of diseases (e.g. monitoring disease progression or regression from one biological state to another); (3) the susceptibility or prediction of response to treatment for a disease; or (4) the evaluation of the efficacy to a treatment for disease. The diagnosis of disease in which the level of the specific gene(s) in the subject can be compared to a baseline or control level in which if the level is above or below the control level, a certain disease is implicated. The prognosis of disease can be assessed by comparing the level of the specific gene biomarker at a first timepoint to the level of the biomarker at a second timepoint which occurs at a given interval after the first timepoint. The prediction of response to treatment for a disease can be determined by obtaining the level of a specific gene biomarker and correlating this level to a gene signature score. The evaluation of the efficacy of the treatment for a disease can be assessed by comparing the level of the specific gene biomarker at a first timepoint before administration of the treatment to the level of the biomarker at a second timepoint which occurs at a specified interval after the administration of the treatment.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzyme-linked immunosorbent assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners.

The terms "diagnosing" or "diagnosis" as used herein refers to the determination of whether a subject comprises a disease or condition such as cancer. "Diagnosing" can also refer to distinguishing one cancer from another.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy such as chemotherapy, such as one or more alkylating agents; radiotherapy; adjuvant therapy; surgery; or a combination thereof in order to optimize therapy for an individual subject. Cancers that express biomarkers that are indicative of a more highly aggressive cancer or poor prognosis may be treated with more aggressive therapies.

The term "treatment" or "treating" as used herein refers to the ability to ameliorate, suppress, mitigate, or eliminate the clinical symptoms after the onset of a disease state. Treatment can include chemicals, such as chemotherapeutic agents or test compounds, and/or non-chemical treatment such as radiation, electrical pulses, and magnetic fields. An effective or successful treatment provides a clinically observable improvement.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes involved in cell cycle regulation, apoptosis, cell proliferation, and angiogenesis.

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease; and a state that is indicative of the efficacy of a treatment of the disease. The biological state may include normal cells or tissues, pre-cancerous cells or tissues, pre-invasive cells or tissues and invasive cells or tissue.

The term "cell" or "cells" is used synonymously herein and refers to in vitro cultures of mammalian cells grown and maintained as known in the art, as well as biological samples obtained from tumor specimens or normal specimens in vivo.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

The term "neoplasia", "cancer", "tumor", "cancerous", and malignant" as used herein, refer to the physiological condition in mammals that is typically characterized by unregulated cell growth or the presence of tumors. The terms are used interchangeably herein. Examples of cancer benefited by the present invention include, but are not limited to, head and neck cancer; lung cancer including non-small cell lung cancer; brain cancer including gliomas; breast cancer; ovarian cancer; endometrial cancer; skin cancer including melanoma; renal cancer; oral cancer; prostate cancer; larynx cancer; thyroid cancer; colon cancer; pancreatic cancer; uterine cancer; cervical cancer; sarcomas; neuroendocrine tumors; leukemias; and gastrointestinal cancers such as cancer of the esophagus, stomach, biliary system, pancreas, small intestine, large intestine, rectum and anus. The invention is particularly of benefit for distinguishing between head and neck squamous cell carcinoma (HNSCC) and primary lung squamous cell carcinoma (LSCC).

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

A "probe set" as used herein refers to a group of one or more polynucleotides that each selectively hybridize to the same target (for example, a specific genomic region or mRNA) that correlates with cancer diagnosis. As such, a single "probe set" may comprise any number of different isolated polynucleotides that selectively hybridize to a given target. A "probe" is a singular polynucleotide that selectively hybridizes to a target.

The term "pre-cancerous" as used herein refers to a physiological condition in mammals that is typically associated with a significantly increased risk of cancer.

The term "pre-invasive" as used herein refers to a physiological condition in mammals that is typically associated with a localized tumor or cancer that has a risk of spreading to other tissues of the body.

The term "invasive" as used herein refers to a physiological condition in mammals that is typically associated with cancer which has spread to multiple locations or tissues in the body. "Metastatic" or "metastasis" also refers to cancer which has spread to multiple locations/tissues.

Patients with HNSCC, who develop a solitary lung nodule diagnosed as squamous cell carcinoma represent a dilemma, where the lung tumor may represent a primary LSCC or metastasis from the patient's HNSCC. The two entities may be distinguished from each other based on various clinical criteria, such as the presence of lymphadenopathy in the neck and multiple bilateral pulmonary nodules, which are suggestive of metastasis. However, when both tumors are histologically similar and no precancerous epithelium, in the form of squamous cell carcinoma in situ is discovered in the vicinity of the lung tumor, a specific diagnosis cannot be rendered. These cases are generally resulted with a differential diagnosis that includes LSCC and metastatic HNSCC, however metastasis from other primary sites cannot be entirely excluded.

The treatment and prognosis of primary LSCC and metastatic HNSCC vary greatly, making it important to differentiate the two entities. The definitive treatment of a solitary primary LSCC is surgical resection, in the form of the lobectomy, along with hilar and mediastinal lymph node dissection. A solitary metastatic nodule of HNSCC can be resected in the form of a wedge resection, in order to preserve as much normal lung parenchyma as possible. Pulmonary metastasectomy is used for metastases. Lymph node dissection in these cases is not performed. The prognosis of patients with a solitary LSCC is better, showing a status post-surgery 5-year survival approaching 80%. Furthermore, adjuvant chemotherapy depending on actionable targets within the tumor and/or immunotherapy are also available for patients with LSCC.

Previous studies have shown that gene expression profiling can be a helpful tool for cancer diagnosis. Micro-array based gene expression profiling has shown highly reproducible results, which along with the use of standardized protocols and array platforms has resulted in significant advances in gene annotation, simultaneously measure the expression of multiple markers. Initial studies used gene expression profiling to distinguish clinically normal tissues from HNSCC and developed highly sensitive and specific predictive models which differentiate HNSCC from dysplastic and normal tissue (Ginos et al., Borczuk et al., Belbin et al).

Other studies went on to detect genetic abnormalities within LSCC and HNSCC to help with distinction. The study by Leong et al. was able to distinguish 13 of their 16 patients with HNSCC and a solitary lung nodule, when they looked at loss of heterozygosity on chromosome arms 3P and 9p. Their evaluation was based on allelic patterns which were discordant or concordant between the index tumor and the lung lesion.

Talbot et al. appears to be the first to use gene expression profiling to distinguish HNSCC from LSCC in 21 lung cancer cases and 31 tongue cancer cases. Their model used hierarchical clustering with 100 to 500 genes but their accuracy decreased when the number of genes was reduced below 100.

Vachani et al. developed a 10-gene classifier based on 28 subjects, which they validated on 122 subjects derived from four independent data sets, with an average accuracy of 96%.

Lal et al. used microarray data files for 76 formalin fixed paraffin embedded tumor specimens. Their classification model measuring the expression of 2600 probe sets showed 82.9% agreement with the known diagnosis in HNSCC and 84.2% in LSCC.

To date, this study is the first to use 306 cases, the highest total number of LSCC and HNSCC for gene expression profiling, over 60,000 probe sets for 25,587 genes and validation against multiple data sets to generate a 22-gene signature for the distinction between HNSCC and LSCC, with a specificity of 100% for LSCC and 91.67% for HNSCC. The current 22-gene signature showed 20 distinct genes and only 2 genes (SFTPB and KRT14) in common with the previous 10-gene classifier (Lal et al). The current study shows the highest possible accuracy for identifying LSCC and the highest possible accuracy seen for identifying HNSCC, which makes it an invaluable clinical tool in the diagnosis and management of these patients.

Materials and Methods

A total of 268 lung SCC samples and 38 head and neck SCC samples from Moffitt Cancer Center Total Cancer Care (TCC) database were used as the training dataset. The gene expression data are on HuRSTA chips, each with 60607 probe sets for 25587 genes. Background correction, normalization, and summarizing of raw microarray data were performed using Robust Multi-Array Average (RMA) algorithm implemented in Bioconductor extensions to the R statistical programming environment.

Tissue samples may be stored by a variety of methods including, but not limited to, fresh frozen, PFA and paraffin embedded.

While the gene expression data was performed on HuRSTA chips, other methods are available including, but not limited to, qPCR (used for quantification of nucleic acids); Affymetrix (used for microarray); and nanostring (used for gene expression assay).

Unpaired t-tests were performed on every gene to identify significantly differentially expressed genes for lung vs. head-and-neck SCC. The top 22 most differentially expressed genes (with p<1.00E-24 adjusted by Bonferroni method) were selected for PCA (Principal Component Analysis) analysis, a linear transformation of the variables into a lower dimensional space which retains maximal amount of information about the variables.

Principal Component Analysis (PCA)

The first and second principal components (PC1 and PC2) of the 22 genes were used as the signature. PCA is mathematically defined as an orthogonal linear transformation that transforms the data to a new coordinate such that the greatest variance by some projection of the data comes to lie on the first coordinate (called the first principal component), the second greatest variance on the second coordinate, and so on. Consider a data matrix X, with column-wise zero empirical mean (the sample mean of each column has been shifted to zero), where each of the n rows represents a different sample, and each of the p columns represents a gene. Mathematically, the transformation is defined by a set of p-dimensional vectors of weights or loadings $W_{(k)} = (W_1, \ldots, W_p)_{(k)}$ that map each row vector $x_i$ of X to a new vector of principal component scores $t_{(i)} = (t_1, \ldots, t_m)_{(i)}$, given by $$t_{k(i)} = x_{(i)} \cdot w_{(k)} \text{ for } i=1, \ldots, n\ k=1, \ldots, m$$

in such a way that the individual variables of t considered over the data set successively inherit the maximum possible variance from x, with each loading vector w constrained to be a unit vector.

First Component

The first principal component of a data vector $x_{(i)}$ can be given as a score $t_{1(i)} = x_{(i)} \cdot w_{(1)}$ in the transformed co-ordinates, where the first loading vector $w_{(1)}$ has to satisfy $$w_{(1)} = \operatorname{argmax}\left\{\frac{w^T X^T X w}{w^T w}\right\}$$

Further Components

The kth component can be found by subtracting the first k−1 principal components from X:

$$\hat{X}_k = X - \sum_{s=1}^{k-1} X w_{(s)} w_{(s)}^T$$

and then finding the loading vector which extracts the maximum variance from this new data matrix $$w_{(k)} = \operatorname*{argmax}_{\|w\|=1}\left\{\|\hat{X}_k w\|^2\right\} = \operatorname{argmax}\left\{\frac{w^T \hat{X}_k^T \hat{X}_k w}{w^T w}\right\}$$

Figure 1:
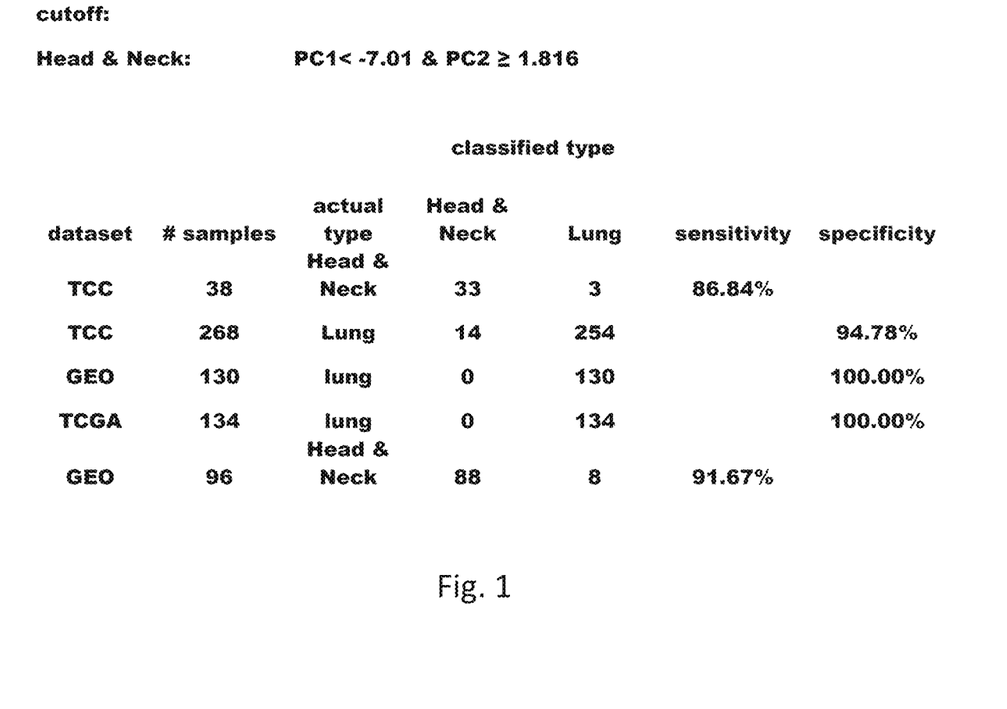
FIG. 1 is a table depicting the cutoff for HNSCC as well as the specificity and sensitivity for each of the five datasets at the optimal cutoffs of first principal component (PCA1) and second principal component (PCA2) for the 22-gene signature.
Figure 2:
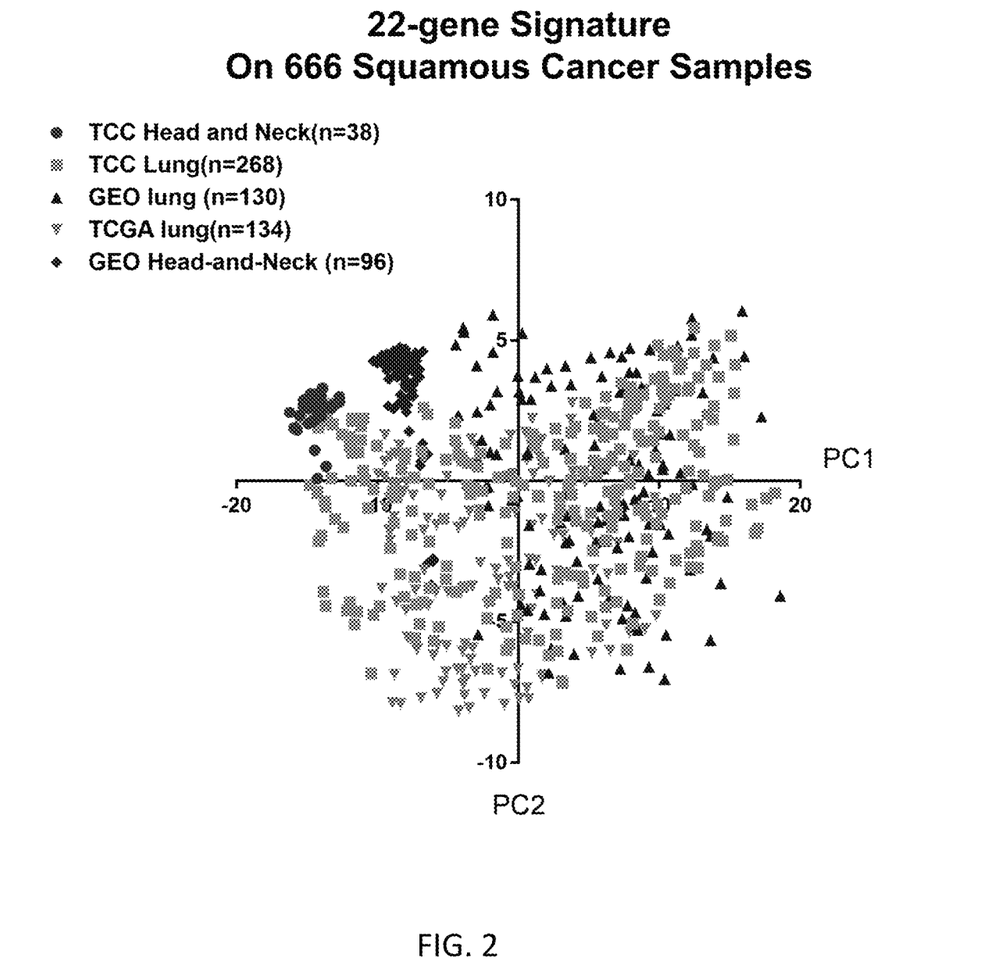
FIG. 2 is a scatterplot depicting PCA1 and PCA2 of the 22 genes for the 666 squamous cell carcinoma cases, including the external data sets (GEO Lung, TCGA Lung, GEO Head and Neck). TCC Head and Neck (n=38) is the 38 SCC head-and-neck samples from TCC database; TCC lung (n=268) is the 268 SCC lung samples from TCC database; GEO lung (n=130) is the 130 SCC lung samples from GSE4573 downloaded from GEO database; TCGA lung (n=134) is the 134 SCC lung cancer samples downloaded from TCGA; and GEO Head-and-Neck (n-96) is the 96 head-and-neck samples from GSE31056 downloaded from GEO database.
Figure 3:
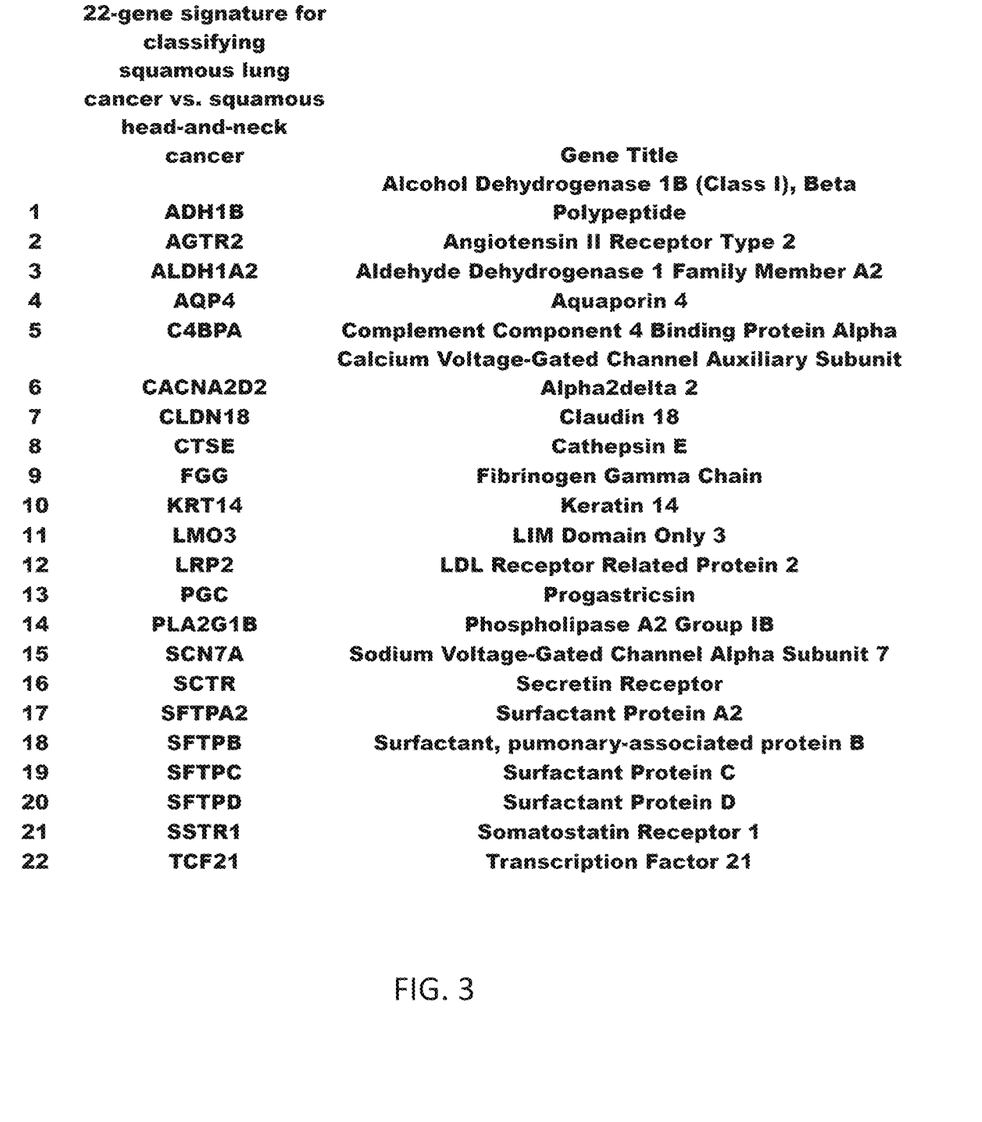
FIG. 3 is a table depicting the 22-gene signature.

The cutoffs of the first and second principal components were selected to maximize the total performance of the signature, i.e., max (sensitivity+specificity), for the training datasets. The cutoff for head-and-neck SCC was set at PC1<−7.01 & PC2≥1.816.

Figure 4:
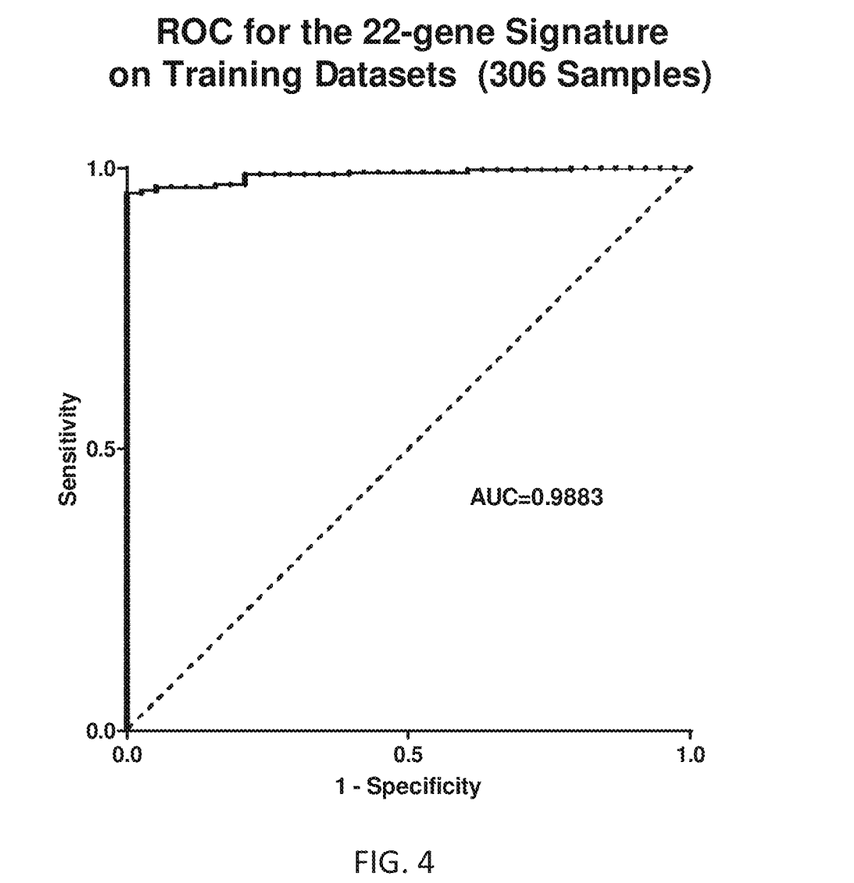
FIG. 4 is a graph depicting the ROC for the 22-gene signature on training datasets (306 samples).

The 22-gene signature was first self-validated on the training dataset with 33 out of 38 correctly classified as "head-and-neck" (sensitivity=86.84%) and 254 out of 268 correctly classified as "lung" (specificity=94.78%). The ROC for the 22-gene signature on the Training datasets had an AUC=0.9883.

Figure 5:
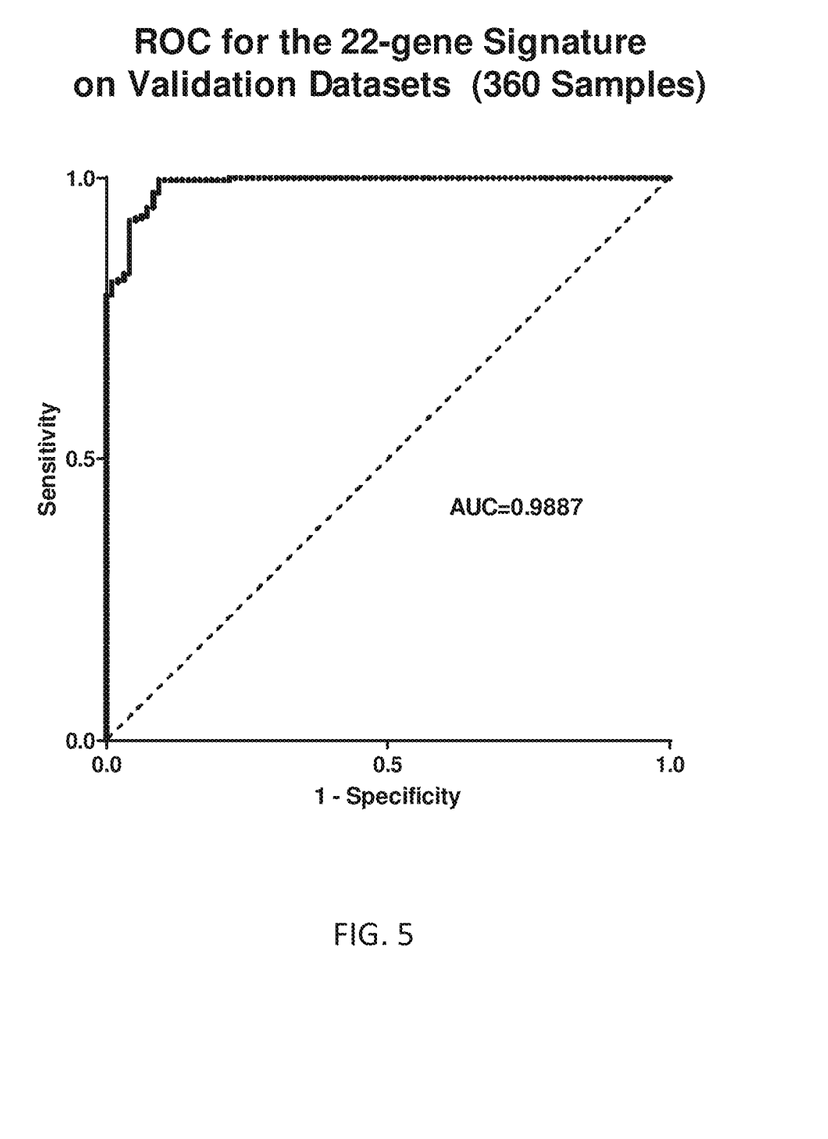
FIG. 5 is a graph depicting the ROC for the 22-gene signature on validation datasets (306 samples).

The signature was further validated on external datasets publicly available at GEO and TCGA databases, with 130 SCC lung cancer samples from GSE4573, 134 SCC lung cancer samples from TCGA and 96 SCC head-and-neck cancer samples from GSE31056, total of 360 samples. The ROC for the 22-gene signature on the Validation datasets had an AUC=0.9887.

To validate the 22-gene signature on external datasets, the inventors first extracted the expression data of the 22 genes from each of the external datasets, centered the gene expressions by the means of the training dataset. The inventors then calculated the first principal component scores (PC1s) and second principal component scores (PC2s) by applying the following formula:

$$t_{k(i)} = x_{(i)} \cdot w_{(k)} \text{ for } i=1, \ldots, n\ k=1, \ldots, m$$

where $X_{(i)}$ is a vector of expression values for gene (i) of the validation dataset and w(k) is a vector of loadings for gene (i) from the training dataset. Finally, the cutoffs obtained from the training dataset were applied to the PC scores of PC1s and PC2s of the validation dataset to classify each sample into SCC lung cancer or SCC head-and-neck cancer.

The signature correctly identified all of the 130 samples of GSE4573 as "lung" (specificity=100%), all the 134 samples of TCGA data as "lung" (specificity=100%), and 88 out of the 96 SCC head-and-neck samples as "head-and-neck" (sensitivity=91.7%).

CONCLUSION

The inventors have developed a way of identifying those patients having lung squamous cell carcinoma from those having head and neck squamous cell carcinoma using a 22-gene signature. This 22-Gene expression profile can assist in distinguishing primary lung SCC from metastatic head and neck SCC. This will make a significant impact on patient management and outcome.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described.

What is claimed is:

1. A method for treating and distinguishing between lung squamous cell carcinoma (LSCC) and head and neck squamous cell carcinoma (HNSCC) in a patient comprising:
obtaining or having obtained a tumor tissue sample from the patient;
diagnosing or having diagnosed the tumor tissue sample as squamous cell carcinoma (SCC);
determining or having determined nucleic acid expression levels of genes ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21 in the SCC sample;
performing or having performed Principal Component Analysis (RCA) on the nucleic acid expression levels of the genes to obtain a first Principal Component Analysis score (PCA1) and a second Principal Component Analysis score (PCA2);
diagnosing the patient with HNSCC if the PCA1 is below −7.01 and the PCA2 is above or equal to 1.816 or
diagnosing the patient with LSCC if the PCA1 is above −7.01 and the PCA2 is below 1.816; and
treating the patient with surgery in the form of a lobectomy with hilar and mediastinal lymph node dissection, adjuvant chemotherapy or immunotherapy if the patient is diagnosed with LSCC or
treating the patient by a pulmonary metastasectomy if the patient is diagnosed with HNSCC.

2. The method of claim 1, wherein the SCC sample is from a solitary lung nodule of the patient.

3. The method of claim 1, wherein the patient has a history of or currently has HNSCC.

4. A method of treating and determining progression of HNSCC in a patient comprising:
obtaining or having obtained a tumor tissue sample from the patient;
diagnosing or having diagnosed the tumor tissue sample as squamous cell carcinoma (SCC);
determining or having determined nucleic acid expression levels of genes ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21 in the SCC sample;
performing or having performed Principal Component Analysis (RCA) on the nucleic add expression levels of the genes to obtain a first Principal Component Analysis score (PCA1) and a second Principal Component Analysis score (PCA2);
determining the HNSCC has progressed from a primary site if the PCA1 is below −7.01 and the PCA2 is above or equal to 1.816; and
treating the HNSCC by pulmonary metastasectomy.

5. The method of claim 4, wherein the SCC sample is taken from a lung.

6. The method of claim 4, wherein the patient previously or currently has HNSCC.

7. A method of determining and treating primary tumor site in a patient having cancer comprising:
obtaining or having obtained a tumor tissue sample from the patient;
diagnosing or having diagnosed the tumor tissue sample as squamous cell carcinoma (SCC);
determining or having determined nucleic acid expression levels of ADH1B, AGTR2, ALDH1A2, AQP4, C4BPA, CACNA2D2, CLDN18, CTSE, FGG, KRT14, LMO3, LRP2, PGC, PLA2G1B, SCN7A, SCTR, SFTPA2, SFTPB, SFTPC, SFTPD, SSTR1, and TCF21 in the SCC sample;
performing or having performed Principal Component Analysis (PCA) on the nucleic add expression levels of the genes to obtain a first Principal Component Analysis score (PCA1) and a second Principal Component Analysis score (PCA2);
diagnosing the patient with primary LSCC if the PCA1 is above −7.01 and the PCA2 is below 1.816; and
treating the LSCC with surgery in the form of a lobectomy with hilar and mediastinal lymph node dissection, adjuvant chemotherapy or immunotherapy.

8. The method of claim 7, wherein the SCC sample is taken from a lymph node or other metastatic site.

9. The method of claim 7. wherein the patient has a history of or currently has HNSCC.

* * * * *